United States Patent

Scoville

[11] 4,256,110
[45] Mar. 17, 1981

[54] DRAINAGE POUCH SYSTEM
[76] Inventor: Alfred M. Scoville, 8005 McKenstry Dr., Laurel, Md. 20810
[21] Appl. No.: 937,790
[22] Filed: Aug. 29, 1978
[51] Int. Cl.³ .............................................. A61F 5/44
[52] U.S. Cl. ................................................... 128/283
[58] Field of Search ............. 128/283, DIG. 24, 214D

[56] References Cited
U.S. PATENT DOCUMENTS

| 2,914,068 | 11/1959 | Schachi | 128/283 |
| 3,713,445 | 1/1973 | Marsan | 128/283 |

Primary Examiner—Robert W. Michell
Assistant Examiner—Thomas Wallen
Attorney, Agent, or Firm—Morton J. Rosenberg

[57] ABSTRACT

A post-surgical drainage pouch system (10) for collection of discharge materials from a body opening (12). Drainage pouch system (10) is locationally mounted adjacent and in contiguous contact with an abdominal wall (14) and is aligned with the body opening (12) formed within the patient. System (10) includes a tubular member (16) which is insertable within a resilient planar member (26). A pouch member (32) is insertable through the tubular member (16) and is captured by an annular disk member (36) in a shoulder portion of the tubular member (16). The drainage pouch system (10) is mounted to the user by a body encircling strap (40) which is releasably coupled to the resilient planar member (26). Subsequent to use, the annular disk member (36) is inserted within an open end section (34) of the pouch member (32) and is disposed of with the discharge material captured within the pouch member (32).

14 Claims, 3 Drawing Figures

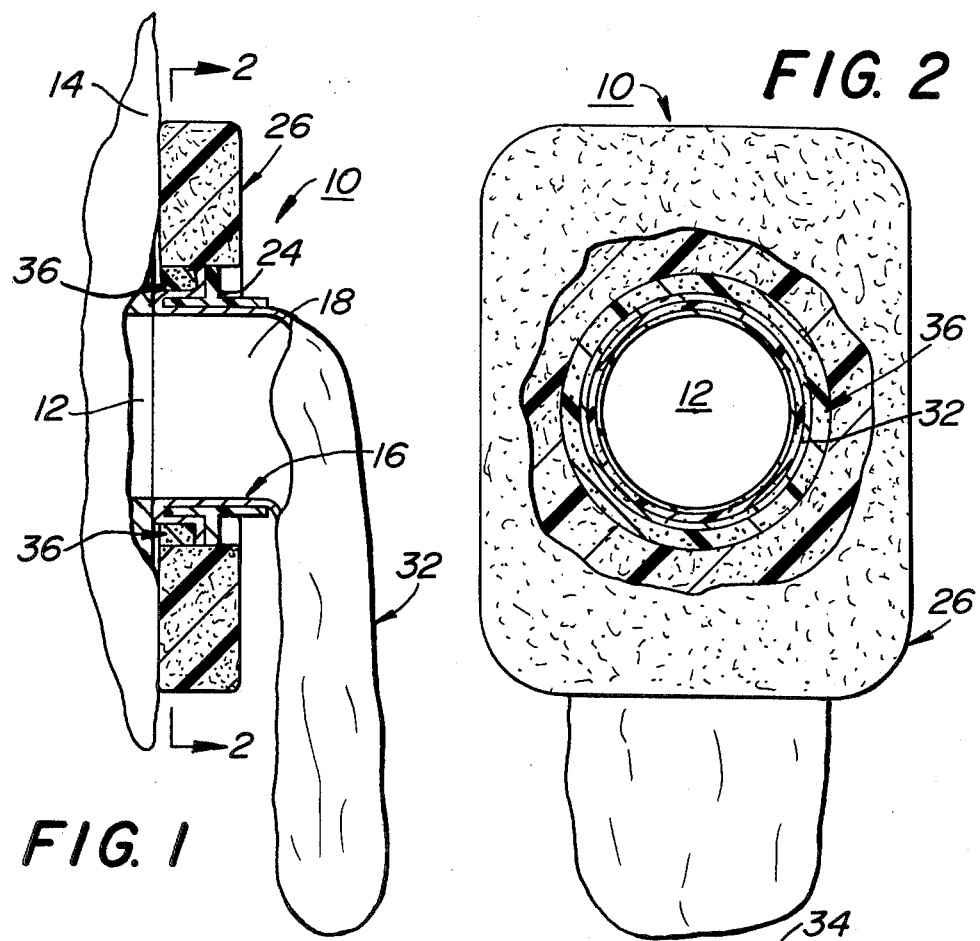
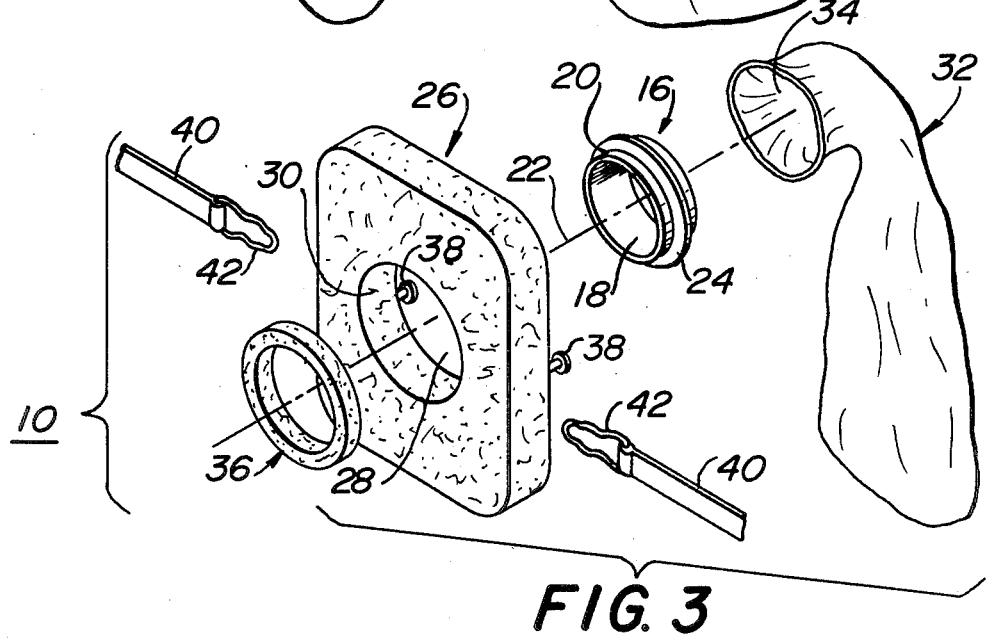

DRAINAGE POUCH SYSTEM

BACKGROUND OF THE INVENTION

1. Field of the Invention

This invention relates to drainage pouch systems adapted for use in connection with discharge materials from the body of a user. In particular, this invention is directed to a drainage pouch system for capturing discharge materials from patients having an ostomy operation. Still further, this invention is directed to a post-surgical drainage pouch system which is locationally mounted in fixed relation in alignment with a stoma. More in particular, this invention pertains to a post-surgical drainage pouch system which is essentially odor free and lightweight for comfort when being maintained on the body of the user. Still further, this invention relates to a post-surgical drainage pouch system which provides for disposable elements in combination with inexpensive and easily attainable pouch members.

2. Prior Art

Colostomy type devices for collection of the discharge materials from the body of a user are known in the art. The best prior art known to applicant includes U.S. Pat. Nos. 3,970,085; 3,856,011; 3,865,109; 3,043,306; 3,006,343; 3,481,336; 3,826,262; 3,964,485; 4,030,500; 3,902,496; 3,897,780; 3,948,256; 3,931,819; 4,054,140; 4,062,361; 3,398,744; and 3,695,268.

Colostomy devices such as that shown in reference U.S. Pat. No. 3,970,085 do include ring portions which are mounted on tubular flanges. Further, such does provide for washer elements, however, such washer interface is generally on the frontal portion of the prior art systems and not adapted for contact with the stoma. Such washer elements are generally not disposable in the nature of the subject invention concept. In such systems, contact with bacteria areas of the body are not provided by disposable elements. Thus, bacteria growth may occur having deleterious effects to the user.

Other prior art colostomy devices such as that shown in reference U.S. Pat. No. 3,856,011 provide for a belt or strap-like holding mechanism, however, the pouch members are maintained by a ring member which is inserted within a peripheral groove formed in a bag holding section. Such prior art systems do not provide for the disposability of bacteria contaminated areas of the colostomy devices.

Other references do not direct themselves to lightweight considerations which aid in the comfort of the user. Additionally, some other prior art references do not direct themselves to the maintenance of the overall pouch system in a stationary mode on the body of the user which may cause misalignment between the stoma and the particular pouch member being utilized. This has the deleterious effect of not capturing all of the discharge material from the body of the user.

Other prior art systems may utilize pouch members which are relatively expensive and not completely disposable at the will of the user. Such may have the disadvantage of forcing the user to utilize such pouch members over a prolonged period of time.

SUMMARY OF THE INVENTION

A post-surgical drainage pouch system for collection of discharge materials from a body opening which includes a tubular member having a through opening. The tubular member includes a flange secured to an outer wall surface of the tubular member where the flange has an outer diameter greater than an outer diameter of the tubular member and forms a shoulder portion of the tubular member. A resilient planar member is included and has a through opening substantially equal to the flange outer diameter. The flange section outer diameter is secured to an inner wall of the resilient planar member through openings. A pouch member having an open end section is insertable through the tubular member opening. A resilient annular disk member is insertable around the tubular member outer wall surface for releasably capturing the pouch open end section between the flange and the resilient annular disk.

An object of this invention is to provide a post-surgical drainage pouch system for collection of discharge materials from a body opening.

Another object of this invention is to provide a drainage pouch system utilized by patients having undergone an ostomy operation.

A still further object of the subject invention is to provide a drainage pouch system which is inexpensive to manufacture and includes disposable elements.

Another object of the instant invention is to provide a drainage pouch system which is maintainable in fixed relation to the abdominal wall of a user during a normal predetermined time interval.

Another object of the subject invention is to provide a drainage pouch system which is lightweight in composition and comfortable for the user during a prolonged period of use.

A still further object of this invention is to provide a drainage pouch system where elements which may be subject to bacteria contamination are disposed subsequent to use.

BRIEF DESCRIPTION OF THE DRAWINGS

FIG. 1 is an elevational sectional view of the post-surgical drainage pouch system in contact with the abdominal wall of a user;

FIG. 2 is a section view of the post-surgical drainage pouch system taken along the section line 2—2 of FIG. 1; and, FIG. 3 is a perspective exploded view of the post-surgical drainage pouch system.

DESCRIPTION OF THE PREFERRED EMBODIMENTS

Referring now to FIGS. 1-3, there is shown post surgical drainage pouch system 10 utilized for collection of discharge materials passing through body openings 12 of a patient. In general, drainage pouch system 10 may be used for collection of discharge materials passing through stoma or body openings 12 where stoma 12 is any artificial permanent opening in abdominal wall 14 made during surgical procedures. In particular, system 10 is adapted for use by a patient who has undergone an ostomy which is an operation to create an artificial anus through abdominal wall 14. The actual surgical formation of the artificial anus is commonly referred to as a colostomy. System 10 is particularly directed to a combination of elements which provides for an overall mounting which remains substantially stationary with respect to movements of the patient for maintaining alignment with stoma 12 during a normal time interval. Additionally, drainage pouch system 10 provides a disposable set of elements which utilizes inexpensive members which allows a simple disposal procedure. Additionally, system 10 allows for a collection system which is substantially odor free during discharge of waste materials through stoma 12 and provides for a system where all elements lying adjacent and contiguous to body opening 12 are easily disposed subsequent to use after a predetermined time interval.

Post-surgical drainage pouch system 10 includes tubular member 16 clearly shown in FIG. 3. Tubular member 16 has through opening 18 passing therethrough. Tubular member 16 is generally cylindrical in contour and has outer wall 20 with a surface defined by an outer diameter of tubular member 16 when taken with respect to an axis line 22 of through opening 18.

Tubular member 16 further includes flange portion 24 which is generally disk-like in contour and is rigidly secured to tubular member outer wall 20 as shown in FIG. 3. Flange section 24 extends in a planar manner having a plane substantially normal to axis line 22. Additionally, flange portion or section 24 has an outer diameter greater than an outer diameter of the tubular member 16. In this manner, a shoulder portion is formed with respect to outer wall 20 and flange portion 24 for purposes to be further illustrated in following paragraphs. Tubular member 16 is generally formed of a rigid material such as a hardened plastic composition. In general, tubular member 16 remains in position adjacent to abdominal wall 14 during use and is generally not a disposable member of drainage pouch system 10. For this reason, tubular member 16 is formed of a lightweight composition material in order that such will be comfortable on the body of the patient during use. If a plastic composition is utilized, tubular member 16 is formed of a closed cell type structure in order that such may be easily cleaned without capturing bacteria which may have a deleterious effect on the patient.

Post-surgical drainage pouch system 10 further includes resilient planar member 26 having through opening 28. Planar member through opening 28 has an internal diameter substantially equal to the external diameter of flange 24 secured to outer wall 20 of tubular member 16. Flange portion 24 is insertable within planar member through opening 28 and is mounted in secured relation to planar member inner wall 30. Securement of flange portion 24 to inner wall 30 may be through friction fit, adhesive bonding, or some like technique, not important to the inventive concept as is herein described, with the exception that once tubular member 16 is insertably mounted in relation to planar member 26, that tubular member 16 be fixedly located.

Planar member 26 lies adjacent and in contiguous contact with abdominal wall 14, as is clearly seen in FIG. 1. Thus, the comfort of the user or patient is of an important nature, in that drainage pouch system 10 is maintained on the body of the user for substantial time inervals. Thus, planar member 26 should be flexible in nature in order to contour itself substantially to the contour of abdominal wall 14 during use. The flexibility is essential due to the fact that abdominal wall 14 deforms during the normal movements of the patient or the user. Additionally, a lightweight construction is important due to the fact that system 10 is maintained essentially throughout a twenty-four hour time interval of each day in aligned positional relation with stoma 12. Still further, planar member 26 should have a relatively high coefficient of friction with respect to abdominal wall 14 in order that normal movements and displacements of abdominal wall 14 will not cause any misalignment of stoma 12 with respect to pouch system 10. For the aforementioned reasons, planar member 26 may be formed of a foam rubber composition and additionally, may be open celled in contour. Any open cell composition has generally a high coefficient of friction and is relatively lightweight in nature. As will be seen, planar member 26 is not generally contiguous with stoma or body opening 12 and thus, the contamination by bacteria from discharge material is minimized.

Pouch system 10 further includes pouch member 32 having open end section 34. Open end section 34 is insertable through tubular member opening 18. Pouch member 32 may be formed of a resilient plastic-like material and may be of the commercial thickness of 2.0 mils, 4.0 mils, or some standard thickness which is commercially available. The commercial availability of pouch member 32 is important in that such plastic-like bag elements are inexpensive to purchase and are easily disposable. Discharge material enters pouch member 32 through open end section 34 and is captured internal to pouch member 32 in the normal fashion. Subsequent to a predetermined time interval of use, pouch member 32 may be disposed of in the normal fashion.

System 10 further includes resilient annular disk member 36 which is insertable around tubular member outer wall 20 and lies contiguous to the shoulder portion formed by flange 24 and outer wall 20. Open end section 34 of pouch member 32 is captured between annular disk member 36 and flange 24 as is shown in FIG. 1.

Thus, in use, pouch member 32 is inserted within opening 18 and extended therethrough. A portion of open end section 34 is wrapped around outer wall 20 and flange 24. Annular disk member 36 is then frictionally forced over outer wall 20 into adjacent relationship with flange 24 for capturing pouch open end section 34 between flange 24 and resilient annular disk 36. Annular disk 36 has an internal diameter slightly greater than the external diameter of tubular member 16 in order to allow a capturing mode of operation. Additionally, annular disk member 36 has an external diameter substantially equal to the internal diameter of planar member through opening 28.

Annular disk 36 as is seen in FIG. 1, lies adjacent and substantially contiguous to abdominal wall 14. Annular disk 36 should be lightweight in construction and have a high coefficient of friction in order to provide a stationary overall system. Annular disk 36 is disposable and thus, may have discharge material contacting therewith from stoma 12. This member 36 may be formed of an open celled, foam rubber type composition for use in pouch system 10.

Subsequent to a predetermined time interval of use, the user may release planar member 26 from adjacent contact relation with abdominal wall 14. Annular disk member 36 is directed internal to open end section 34 for insert into pouch member 32 with the discharge material collected during the predetermined time interval. Open end section 34 is then closed by the user and the combination of pouch member 32 and annular disk 36 is disposed of. Subsequently, the patient utilizes a new pouch member 32 in combination with a new resilient annular disk member 36 for the next predetermined time interval. In this manner, bacteria growth is minimized during use of system 10.

Drainage pouch system 10 further includes a mechanism for releasably securing system 10 to the body of the user. The releasable securement mechanism includes stud type members 38 which are secured to resilient planar member 26 on opposing transverse sides thereof. Stud members 38 may be of the rivet type or some like member. Strap member 40 is releasably fastened to stud members 38 and is adapted to encircle the body of a user. Strap members 40 may be adjustable as is common in a number of such belt or strap member systems. Each end of strap member 40 includes hook members 42 fastened on opposing ends of strap member 40 for securing strap member 40 to stud members 38. As is a normal mode of attachment, hook members 42 are passed over the heads of stud members 38 and releasably secure system 10 to the body of the user.

It is to be understood that drainage pouch system 10 as has hereinbefore been described, provides for a maximization in the ease of disposability subsequent to use. Annular disk member or washer 36 is pushed through opening 28 internal to pouch member 32 after use and the entire pouch member 32 and disk member 36 may be closed and disposed of in a simple fashion. Thus, there is no contamination with the body of the user, and waste material being disposed of. Further, utilization of annular disk member 36 and pouch member 32 in combination provides for a close interface with the body of the user and greatly reduces gaseous odors eminating from the body of the user.

It is to be understood that other modifications may be resorted to without departing from the spirit or scope of the invention as has hereinbefore been described. Equivalent elemental structures may be substituted for those specifically shown and described, certain features may be used independently of other features, and in some cases, portions or elements may be reversed, all without departing from the spirit or scope of the invention. It is to be understood that the invention is therefore only limited by the claims appended hereto.

What is claimed is:

1. A post-surgical drainage pouch system for collection of discharge materials from a body opening, comprising:
    (a) an extended tubular member having a through opening, said tubular member including a flange secured to an outer wall surface intermediate said extension of said tubular member, said flange having an outer diameter greater than an outer diameter of said tubular member forming a shoulder portion;
    (b) a resilient planar member having a through opening substantially equal to said flange outer diameter, said flange being secured to an inner wall of said resilient planar member through opening;
    (c) a pouch member having an open end section, said open end section being insertable through said tubular member opening; and,
    (d) a resilient annular disk member insertable within said planar member through opening and around said tubular member outer wall surface within said shoulder portion for releasably capturing said pouch open end section between said flange and said resilient annular disk.

2. The post-surgical drainage pouch system as recited in claim 1 where said tubular member is formed of a rigid material.

3. The post-surgical drainage pouch system as recited in claim 2 where said tubular member rigid material is plastic.

4. The post-surgical drainage pouch system as recited in claim 1 where said resilient annular disk matingly engages said shoulder portion of said tubular member.

5. The post-surgical drainage pouch system as recited in claim 4 where said resilient annular disk is insertable within said planar member through opening for mating engagement with said shoulder portion of said tubular member.

6. The post-surgical drainage pouch system as recited in claim 1 where said resilient planar member includes a surface area substantially greater than said planar member through opening.

7. The post-surgical drainage pouch system as recited in claim 1 where said resilient planar member is formed of a foam rubber composition.

8. The post-surgical drainage system as recited in claim 1 where said pouch member is formed of a plastic composition.

9. The post-surgical drainage pouch system as recited in claim 1 where said resilient annular disk member is formed of a foam rubber composition.

10. The post-surgical drainage pouch system as recited in claim 9 where said resilient annular disk member is deformable for insert into said pouch member open end section subsequent to use.

11. The post-surgical drainage pouch system as recited in claim 10 where said resilient annular disk is disposably displaced internal said pouch member subsequent to use.

12. The post-surgical drainage pouch system as recited in claim 1 including means for releaseably securing said pouch system to the body of a user.

13. The post-surgical drainage pouch system as recited in claim 12 where said securement means includes:
    (a) a pair of stud members secured to said resilient planar members; and,
    (b) a strap member releasably fastened to said stud members, said strap member for substantially encircling the body of a user.

14. The post-surgical drainage pouch system as recited in claim 13 where said strap member includes hook members fastened on opposing ends of said strap member for securing said strap member to said stud members.

* * * * *